United States Patent

DeFreez et al.

[11] Patent Number: 5,946,092
[45] Date of Patent: Aug. 31, 1999

[54] DUAL LASER HETERODYNE OPTICAL PARTICLE DETECTION TECHNIQUE

[75] Inventors: Richard K. DeFreez, Azalea; Kenneth L. Girvin; Mingguang Li, both of Grants Pass, all of Oreg.

[73] Assignee: Pacific Scientific Instruments Company, Grants Pass, Oreg.

[21] Appl. No.: 09/200,206

[22] Filed: Nov. 25, 1998

Related U.S. Application Data

[63] Continuation-in-part of application No. 09/032,257, Feb. 27, 1998.

[51] Int. Cl.$^6$ .................................................. G01N 15/02
[52] U.S. Cl. .......................................... 356/336; 356/339
[58] Field of Search ............................. 356/336, 338, 356/339, 340, 343, 345, 349; 372/22, 97; 250/222.2

[56] References Cited

U.S. PATENT DOCUMENTS

| | | | |
|---|---|---|---|
| 4,242,194 | 12/1980 | Steiner et al. | 356/337 |
| 4,571,079 | 2/1986 | Knollenberg | 356/336 |
| 4,594,715 | 6/1986 | Knollenberg | 372/32 |
| 4,798,465 | 1/1989 | Knollenberg | 356/336 |
| 4,893,928 | 1/1990 | Knollenberg | 356/336 |
| 5,135,304 | 8/1992 | Miles et al. | 356/338 |
| 5,642,193 | 6/1997 | Girvin et al. | 356/339 |

OTHER PUBLICATIONS

R. J. Nordstrom, L. J. Berg, "Coherent Laser Radar: Techniques And Applications," *Lasers & Optronics*, Jun. 1990, pp. 51–56.

*Primary Examiner*—Hoa Q. Pham
*Attorney, Agent, or Firm*—Stoel Rives LLP

[57] ABSTRACT

A gas-borne optical scattering particle counter uses intracavity optical scattering and heterodyne detection techniques to overcome the lower limit on particle size detection stemming from background light scattering by the gaseous carrier in which a particle is immersed. The particle counter uses a heterodyne technique to exploit a basic physical difference between target particle scattered light and the background light. The carrier gas molecules have a pronounced temperature-induced Maxwell-Boltzmann translational velocity distribution and an associated Doppler broadened spectral scattering characteristic that are dissimilar to those of the target particle. The Doppler broadened background Rayleigh light is orders of magnitude spectrally wider than that scattered by a particle in a particle detector view volume. This difference in bandwidth allows the local oscillator light to "tune in" the target particle light in a beat frequency signal and "tune out" the background radiation. In this way, most of the Rayleigh scattered light signal can be removed from the total signal, leaving a dominant target particle signal. To develop sufficient local oscillator power, an embodiment using intracavity optical scattering and heterodyne detection techniques is implemented in a dual laser configuration in which a first laser serves for intracavity light scattering and a second laser functions as the local oscillator. The first and second lasers are frequency locked to maintain a substantially constant frequency difference between them and thereby obtain a stable beat frequency signal. The beat frequency signal is proportional to the square root of the product of the target particle signal optical power and the local oscillator power and can be many orders of magnitude larger for coherent (i.e., heterodyne) detection than the scattered light signal for direct optical detection.

20 Claims, 5 Drawing Sheets

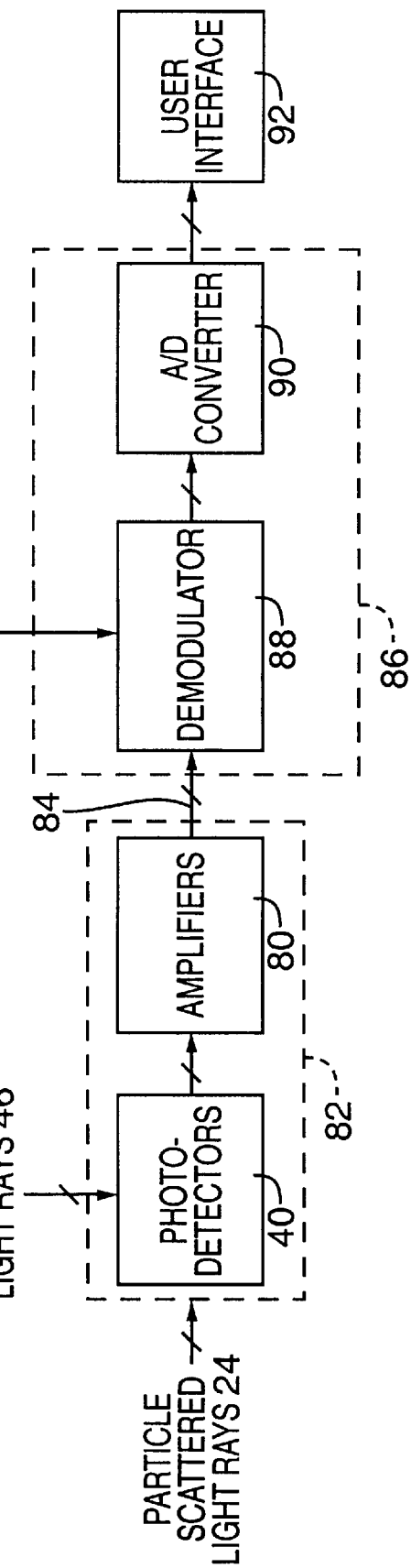

DUAL LASER HETERODYNE OPTICAL PARTICLE DETECTION TECHNIQUE

RELATED APPLICATION

This is a continuation in part of application Ser. No. 09/032,257, filed Feb. 27, 1998.

TECHNICAL FIELD

The present invention relates to optical particle detection and, in particular, to fluid-borne particle detection implemented with a dual laser-based heterodyne optical detection technique that effectively discriminates between target particle scattered light and background light to increase particle size detection sensitivity.

BACKGROUND OF THE INVENTION

Contamination control, including gas-borne and liquid-borne particulate monitoring, plays a critical role in the manufacturing processes of several industries. These industries require cleanrooms or clean zones with active air filtration and require the supply of clean raw materials such as process gases, de-ionized water, chemicals, and substrates. In the pharmaceutical industry, the Food and Drug Administration requires particulate monitoring because of the correlation between detected particles in an aseptic environment and viable particles that contaminate the product produced. Semiconductor fabrication companies require particulate monitoring as an active part of quality control. As integrated circuits become more compact, line widths decrease and wafer sizes increase such that the sizes of particulates causing quality problems become smaller. Detection of particles in liquids, especially in water, is also of great importance for environmental protection.

To perform particulate monitoring, currently available commercial submicron particle sensors use direct optical detection techniques to determine the presence, size, and/or number of particles. The detection and discrimination of 0.08 μm particles is the highest sensitivity currently achievable by direct optical detection techniques for airborne particle counting and/or sizing at a typical sample flow rate of 1.0 cubic foot per minute. This sensitivity is achieved by employing optical scattering from He—Ne laser intracavity light. The 0.08 mm particle detection size limit for gas-borne particle detection stems from strong background Rayleigh (molecular) scattering in gases. The detection and discrimination of 0.05 μm particles is the highest sensitivity currently achievable by direct optical detection techniques for liquid-borne particle counting and/or sizing at a typical sample flow rate of 4 milliliters/minute. The 0.05 μm particle detection size limit for liquid-particle detection stems from strong Brillouin scattering in water. One manufacturer, Particle Measuring Systems, Inc., Boulder, Colo., uses in its Micro LPC-H airborne particle detector and in its Micro DI50 liquid particle detector a direct optical detection technique to produce these particle sensitivities. These latter sensitivities are state of the art for commercial particle detectors, but they are not recent developments.

The basic building block for this technology is optical scattering of laser light and direct detection of the optical signal scattered by the particles. Because the optical signal scattered by submicron particles has a small scattering cross-section, high incident optical intensities are necessary to achieve detectability. In the past for gas-borne particle detectors, the economical and practical approach to achieving the required optical intensity levels (on the order of 10,000 watts/cm²) was to use a multilongitudinal mode and multilateral mode He—Ne laser. Such lasers exhibit, however, significant amounts of noise, some of which is cancellable by complicated noise cancellation schemes and some of which is not cancellable. Noise cancellation schemes typically entail the use of extra optical detectors to monitor the fluctuations of the intracavity optical intensity so that their effects might be removed from the weak particle signal. Moreover, multimode lasers are implemented with brute force direct optical detection. For liquid-borne particle detectors, the economical and practical approach to achieving the required optical intensity levels was to use a focused laser (typically diode laser) beam, thereby increasing local optical intensity while reducing the background scattering by reducing the size of the view volume containing the particle. The reduction of the view volume had, however, the undesirable effect of simultaneously reducing the sample rate.

Although these cumbersome methods have had significant success leading to the detectability levels described above, there is a fundamental inherent limit to the direct detection method that has prevented any recent significant advance in particle detection sensitivity. Background scattering limits the minimum particle size sensitivity achievable by lasers using direct optical detection techniques. The standard approach, which was developed during the late 1980's, to overcoming shot noise associated with the background light was to minimize the view volume a given detector sees. For gas-borne detection this approach was implemented by division of the total sample view volume into as many as possible subvolumes by the use of arrays of photodiode detectors, each photodiode detector viewing only one subvolume and thus a smaller amount of background noise. For liquid-borne particle detectors the view volume was decreased using a focused laser beam as described above. This became and has since remained the state of the art.

Several drawbacks of the He—Ne laser limit its performance as a tool for optical detection of particles. Of the several drawbacks, three are immediately obvious. First, the He—Ne laser has an intrinsically low gain and, therefore, is susceptible to minor intracavity losses such as contamination from the ambient environment it is meant to sample. Second, the He—Ne laser employs high voltages, typically on the order of 2 kV. Third, the electrically charged window on the He—Ne laser tube attracts contamination in a manner similar to the way a computer monitor or television screen does.

As mentioned above, current optical scattering particle counters use photodiodes to implement direct optical detection techniques. For such direct optical detection, the signal-to-noise power ratio at the amplifier output is given by (A. Yariv, *Optical Electronics,* Holt, Reinhart, and Winston, 1985, 3rd Edition)

$$\frac{S}{N} = \frac{2(Pe\eta/h\nu)^2}{3e^2(P+P_B)\eta\Delta\nu/h\nu + 2ei_d\Delta\nu + 4kT_e\Delta\nu/R_L}, \quad (1)$$

where P is the optical signal power resulting from scattering by a particle of interest, e is the electronic charge, η is the detector quantum efficiency (i.e., the average number of carriers generated for an incident photon), h is Planck's constant, ν is the optical carrier frequency, $P_B$ is the background optical signal power, $i_d$ is the diode photodetector dark current, Δν is the frequency bandwidth of the detection electronics, k is Boltzmann's constant, and $T_e$ is the effective temperature chosen so that the last term in the denominator accounts for the thermal noise of the load, $R_L$, across the detector as well as for the noise generated by the amplifier that follows the detector. The denominator in equation (1) contains four terms, each representing an independent noise source. The first term represents signal shot noise, which cannot be eliminated. The second term is caused by background radiation shot noise. The third term is the result of detector dark current, and the fourth term represents noise caused by the load resistance, $R_L$, across the output of the photodiode and the amplifier following the detector.

It is well known that the signal-to-noise ratio and thus the lower limit on the particle size for gas-borne particle counters is limited by background noise generated by Rayleigh scattering from the gas carrier in which the particle is immersed. The signal-to-noise ratio and thus the lower limit on the particle size for liquid-borne particle counters is about the same as that of gas-borne particle counters but results from strong Brillouin scattering in liquids such as water.

This situation is called "background shot noise limited" because the shot, or quantum, noise associated with the background radiation is the major source of noise in the optical detection system. An ideal detection system would be one in which the particle size detection sensitivity is at the signal quantum noise detection limit. The practical achievement of this limit using direct optical detection is infeasible because it would depend on total suppression of other noise sources, such as detector dark current, in addition to the background signal.

SUMMARY OF THE INVENTION

An object of the invention is, therefore, to provide a method and system that is characterized by increased particle size detection sensitivity.

The present invention implements highly sensitive optical scattering and heterodyne detection techniques for gas-borne and liquid-borne particle counting. Preferred implementations for gas and liquid carrier media embody heterodyne detection.

Preferred embodiments of the present invention for gas-borne particle detection use intracavity optical scattering and heterodyne detection techniques to overcome the lower limit on particle size detection stemming from background optical noise generated from Rayleigh scattering by the gas carrier in which a particle is immersed. The invention is embodied in an optical scattering particle counter that uses a heterodyne technique to exploit a basic physical difference between target particle scattered light and the background light. The carrier gas molecules have a pronounced temperature-induced Maxwell-Boltzmann translational velocity distribution and an associated Doppler broadened spectral scattering characteristic that are dissimilar to those of the target particle. The Doppler broadening of the optical scattering from the carrier gas, which is typically air, is exploited to significantly reduce the relative background light noise seen by a photodiode detector.

This may be accomplished using an offset homodyne detection technique implemented, for example, with a He—Ne laser gain medium, but the preferred embodiments are implemented with a diode-laser-pumped solid-state laser. A spectrally narrow optical output leaks from one of two laser resonator mirrors and is used as a local oscillator beam against which to beat light scattered by the target particle and light signal resulting from background Rayleigh scattering. The Doppler broadened background Rayleigh light is orders of magnitude spectrally wider than that scattered by a particle in a particle detector view volume. This difference in bandwidth allows the local oscillator light to "tune in" the target particle light in a beat frequency signal and "tune out" the background radiation. In this way, most of the Rayleigh scattered light can be removed from the total signal, leaving a dominant target particle signal.

The use of a very high reflectivity (99.999%) intracavity mirror from which the optical output leaks can provide a local oscillator beam of insufficient power to achieve local oscillator shot noise limited detection. To develop sufficient local oscillator power, an embodiment using intracavity optical scattering and heterodyne detection techniques is implemented in a dual laser configuration in which a first laser serves for intracavity light scattering and a second laser functions as the local oscillator. The first and second lasers are frequency locked to maintain a substantially constant frequency difference between them and thereby obtain a stable beat frequency signal.

Preferred embodiments of the present invention for liquid-borne particle detection use external-to-cavity optical scattering and heterodyne detection techniques to overcome the lower limit on particle size detection stemming from background optical noise generated primarily by Brillouin scattering by the liquid carrier in which a particle is immersed. The Brillouin broadening of the background light significantly reduces relative background light noise seen by the photodetector.

This may be accomplished using an offset homodyne detection technique implemented, for example, with a diode laser operating in a single longitudinal mode as a light source for homodyne detection of particles outside of a laser cavity. Although external-to-cavity detection produces lower intensity particle-scattered laser light, the highly sensitive homodyne detection technique discriminates against a frequency shift of the Brillouin scattering, which is often above 6 GHz and therefore substantially greater than the 3 MHz nominal signal bandwidth. The relative background noise current caused by Brillouin scattering can, therefore, be nearly completely eliminated by filtering to thereby enable achievement of about 0.04 μm particle size sensitivity at increased sample flow rates, which is far superior to currently available water-particle sensors. Although there are no cavity mirror attenuation effects in external-to-cavity detection, a dual laser configuration could also be implemented in liquid-borne particle detection.

Reduction of the background radiation signal and proper optical detector and signal amplifier designs cause the signal-to-noise power ratio to become local oscillator shot noise limited for a heterodyne system and is expressed as $$\frac{S}{N} = \frac{\eta P_S}{h \nu \Delta \nu}, \quad (2)$$

where the symbols are the same as those defined above for equation (1) except that the subscript "s" has been added to emphasize that the signal-to-noise ratio is limited only by the particle signal itself. The beat frequency signal power represents the size of a target particle, and recurrences of the beat frequency signal represent the number of target particles.

The beat frequency signal not only reduces the relative background noise but also increases the signal representing the target particle light. With heterodyne detection, the beat frequency signal is proportional to the square root of the product of the target particle signal optical power and local oscillator beam optical power. Because the local oscillator beam optical power can be many orders of magnitude greater than the target particle signal optical power, the beat frequency signal can be orders of magnitude larger for coherent (i.e., heterodyne) detection than the scattered light signal for direct optical detection.

In one, relatively simple, embodiment, amplitude modulation of the scattered intensity from the particle as it traverses the beam creates a side-band frequency that can be used to shift the detection frequency away from 0 Hz. In a second, slightly more complicated, embodiment, an amplitude or phase shifter placed in the path of the local oscillator beam induces an additional frequency shift.

Additional objects and advantages of this invention will be apparent from the following detailed description of preferred embodiments thereof which proceeds with reference to the accompanying drawings.

BRIEF DESCRIPTION OF THE DRAWINGS

FIG. 4 is a block diagram showing the processing of signals derived from particle scattered light rays and reference light rays in accordance with the heterodyne technique of the invention.

DETAILED DESCRIPTION OF PREFERRED EMBODIMENTS

Figure 1:
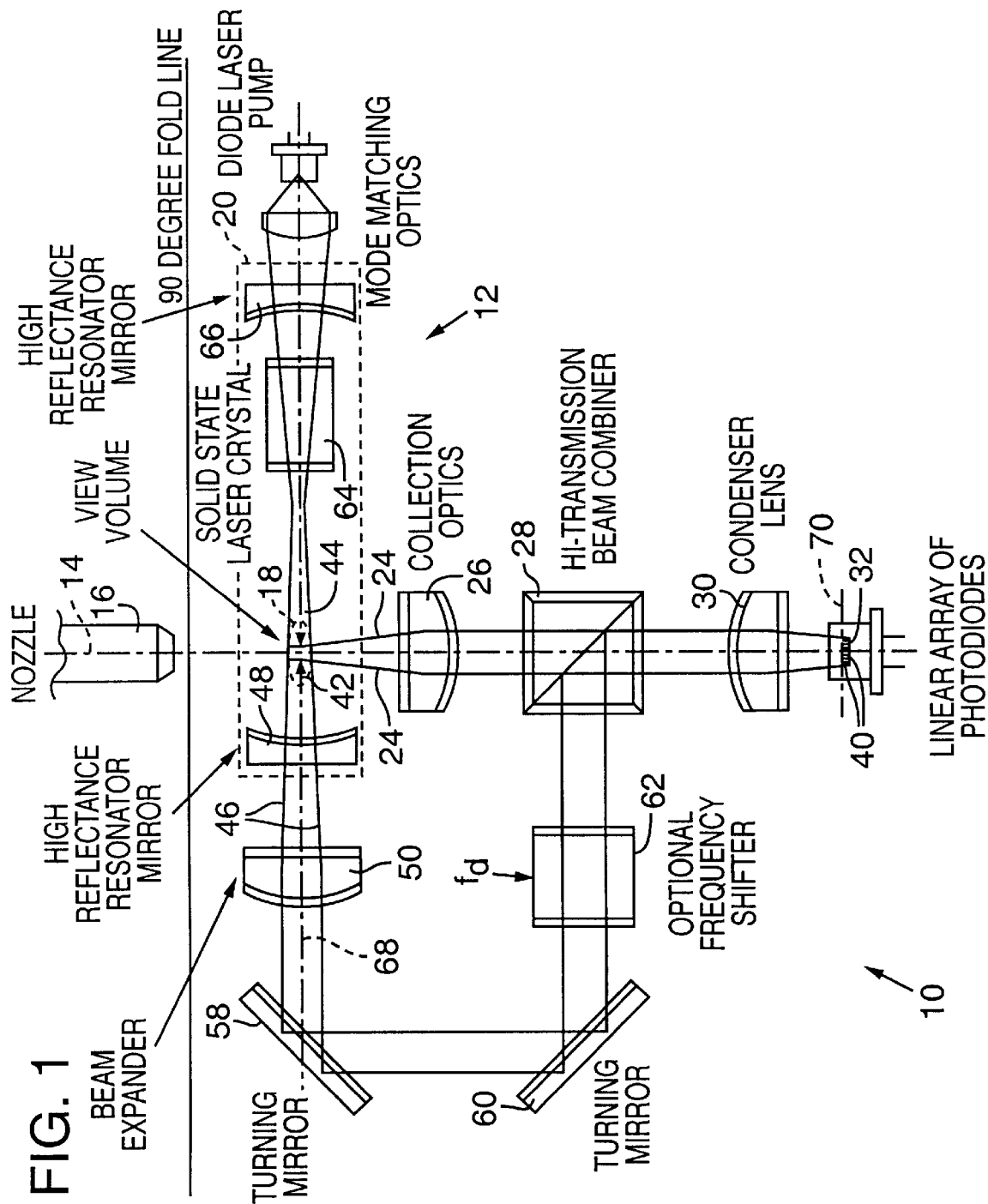
FIG. 1 is a block diagram of an ultra-high sensitivity gas-borne particle counter using multi-channel heterodyne detection.

Particle detection using intracavity optical scattering and heterodyne detection techniques is described with reference to FIG. 1, which shows a gas-borne particle counter 10 that performs heterodyne detection of small particles. Particle counter 10 includes a diode laser-pumped, high intracavity power solid-state laser 12, which is robust, efficient, compact, operates in the absence of high voltages, and can be constructed to have the high beam and spectral qualities required for efficient heterodyne detection. (The invention could also be practiced with the use of a gas or dye laser.) The intracavity optical power scatters radiation both from particles injected in a flow direction 14 by a nozzle 16 and from the gases within a view volume 18 in a resonator 20 of laser 12. Scattered light rays 24, including Doppler broadened background Rayleigh light, are collected and collimated by collection optics 26, transmitted through a beam combiner 28, and then imaged by a condenser lens 30 onto a linear array 32 of photodiode detectors 40. Each photodiode detector 40 of array 32 detects the scattered light rays 24 from a small length 42 along an intracavity beam 44 in view volume 18. A small amount of light 46 simultaneously leaks out of a left-hand side resonator mirror 48 and is collected, expanded, and collimated by a beam expander 50. An expanded beam of light 46 is then redirected by a pair of turning mirrors 58 and 60 to beam combiner 28 from which it collinearly copropagates to condenser lens 30 where it is focused onto linear array 32 of photodiode detectors 40.

The technique implemented by particle counter 10 is called a self-heterodyne or "homodyne" method because it uses the same optical oscillator to generate the signal (particle scattered light rays 24) and the local oscillator (leaked laser light 46). Heterodyne detection entails developing a beat frequency signal between the particle scattered light signal and the local oscillator in a square-law detector which is, in this case, a photodiode detector 40. The beat frequency is selectively detected to the exclusion of other beat frequencies. The beat frequency for self-heterodyne detection is at zero frequency, i.e., a DC signal, which is known to be a particularly undesirable detection frequency, for example, because of 1/f noise. Shifting the beat frequency to some nonzero value in accordance with what is called an offset heterodyne technique eliminates the DC noise problem. Offset heterodyne detection can be accomplished by direct frequency shifting by means of a frequency shifter 62 shown in FIG. 1 and by indirect methods. Amplitude modulation of light rays 24 scattered by a particle traveling through intracavity beam 44 is an example of an indirect method that will induce a frequency shift which can be used for indirectly offsetting the heterodyne signal. The preferred embodiment described herein is implemented with direct frequency shifting by frequency shifter 62 and will be referred to simply as a heterodyne detection process. A preferred frequency shifter 62 is an acousto-optic modulator receiving a drive signal, $f_d$, that provides the offset frequency.

Skilled persons will appreciate that the intracavity modal structure required for heterodyne detection has quite different spectral and spatial properties from those of conventional high intracavity-power He—Ne laser-based particle detectors. The latter lasers contain multilongitudinal spectral and multilateral spatial modes that result in temporal and spatial optical chaos (optical turbulence noise). Heterodyne detection uses single spectral and spatial mode performance for efficient operation. A preferred embodiment uses a high intracavity power, lowest order Gaussian mode derived from a half-symmetric spherical mirror resonator (not shown).

Laser resonator 20 contains a Cr:LiSAF crystal 64 and curved resonator mirrors 48 and 66 with HR coatings (R~0.999965) to provide high power in a fundamental Gaussian mode. This configuration nearly minimizes the number of optical elements and optical surfaces in resonator 20 and thus nearly minimizes the round-trip scattering and absorption losses. Single longitudinal mode control for a Cr:LiSAF lasing medium may require use of a spectral narrowing element in resonator 20 or use of injection locking to compensate for an insufficient etalon effect of the Cr:LiSAF crystal. The reason is that an insufficient etalon effect coupled with high scattering losses associated with Cr ion concentrations may not allow sufficient pump absorption in a Cr:LiSAF crystal of sufficiently short length to have an etalon-free spectral range that exceeds the spectral gain bandwidth of the Cr ion. For Nd:YVO$_4$, however, the crystal itself can be used as the etalon because the gain bandwidth is only 0.9 nm (as compared with several hundred nanometers for the Cr ion).

Particle counter 10 is preferably designed for detection efficiency and high carrier gas flow rate. The efficiency of a heterodyne detection system is inversely proportional to its angular field of view. This is true because the optical heterodyne efficiency is inversely proportional to the integral of the phase difference between the local oscillator field and scattered signal wavefronts over the surface of a photodiode detector 40. In short, large detectors lead to larger integrals or lower strength heterodyne signals. On the other hand, the flow rate of intracavity particle counter 10 is proportional to the width of view volume 18. The configuration of particle counter 10 in FIG. 1 also employs a linear array 32 of photodiodes 40 effectively creating many parallel heterodyne detection channels, which allow for a total view volume 18 while maintaining the efficiency of the heterodyne detection process.

The heterodyne method uses linear array 32 of photodiode detectors 40 with total dimensions that are proportional to the image dimensions of view volume 18. Array 32 is arranged such that scattered light from each particle passing through view volume 18 is imaged onto the one detector 40 corresponding to that area of view volume 18. The height of detector 40 is proportional to the distance the particle travels through view volume 18. The length of array 32 is the total of the widths of detectors 40 and the minimal spacing between them. The detector dimensions are minimized to provide increased phase overlap between particle scattered light rays 24 and reference light rays 46 and to lower the detector capacitance.

FIG. 4 shows in block diagram form the processing of signals derived from particle scattered light rays 24 and reference light 46. With reference to FIG. 4, each detector 40 is connected to an amplifier 80 to form a photo-amplifier 82. Each photo-amplifier 82 receives two optical carriers, one from particle scattered light rays 24 and one from reference light 46. The combined light, in the case of the "offset heterodyne" technique, has a DC magnitude and a dominant beat frequency. The particle-scattered light carrier then becomes directly amplitude modulated as a particle traverses the laser beam. The resulting amplitude modulation of the dominant beat frequency contains particle sizing information. Each photo-amplifier 84 output is post-processed by processing circuitry 86, which includes demodulation electronics 88 and an analog-to-digital converter 90, to extract the signal amplitude representing the particle scattered light. The drive signal, $f_d$, applied to frequency shifter 62 to provide the offset frequency can be used by demodulation electronics 88 to tune-in the resulting optical carrier beat frequency. Analog-to-digital converter 90 converts the extracted signals to digital signals. The signal amplitude of the extracted signal represents the size of the particle. Repetitive signals represent the number of particles.

The resulting signals are directed to a user interface 92, as is typically done in conventional particle counters. The digital signals represent the size and number of the particles that pass through view volume 18.

In direct light scatter collection systems, the relationship of particle size to optical size is proportional to $d^6$, where d is the particle diameter. These detection methods have limits to the dynamic range of their output. The particle size to signal relationship in heterodyne detection is proportional to $d^3$. The heterodyne detection has the added advantage of increased dynamic range of particle size detection by a power of two.

As indicated above, the spectrally narrow light 46 that leaks from laser resonator mirror 48 are used as a local oscillator beam against which to beat light rays 24 scattered from a target particle and light from background Rayleigh scattering. In this way, most of the Rayleigh light can be removed from the scattered light rays 24, leaving a dominant particle signal. The Doppler broadened background Rayleigh light is orders of magnitude spectrally wider than that scattered by a particle in view volume 18, thus allowing the local oscillator light to "tune in" the target particle light and to "tune out" the background radiation of light rays 24.

Figure 2A:
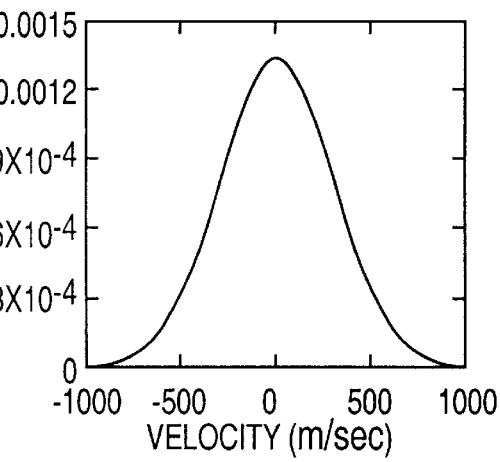
FIGS. 2A and 2B show the molecular velocity probability density and a combined molecular Doppler shift, respectively, for a nitrogen carrier gas.
Figure 2B:
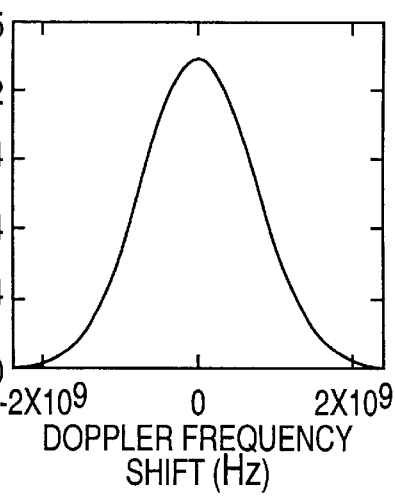

The calculated relative Doppler-induced spectral widths of the radiation scattered from background molecules and a target particle are shown in FIGS. 2A, 2B, 3A, and 3B. FIG. 2A shows the calculation of the room-temperature molecular velocity probability density (Maxwell-Boltzmann distribution) for a nitrogen carrier gas, which is used for convenience because air is about 80 percent nitrogen. A large portion of these molecules has very high translational velocities. FIG. 2B shows the molecular frequency probability density of Doppler-induced frequency shifts. FIGS. 2A and 2B show that the Rayleigh background noise has a spectral width of over 2 GHz.

Figure 3A:
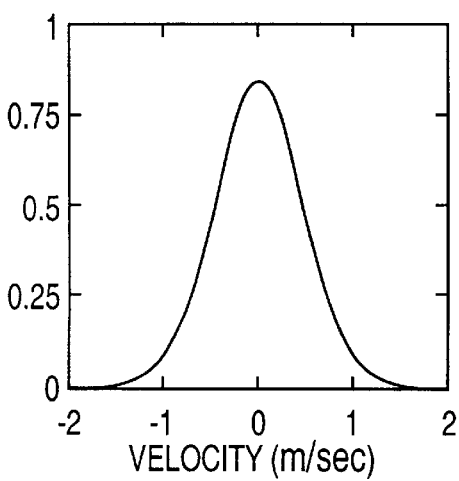
FIGS. 3A and 3B show the particle velocity probability density and a combined Doppler shift, respectively, for silicon spheres having a 12.5 nm radius.
Figure 3B:
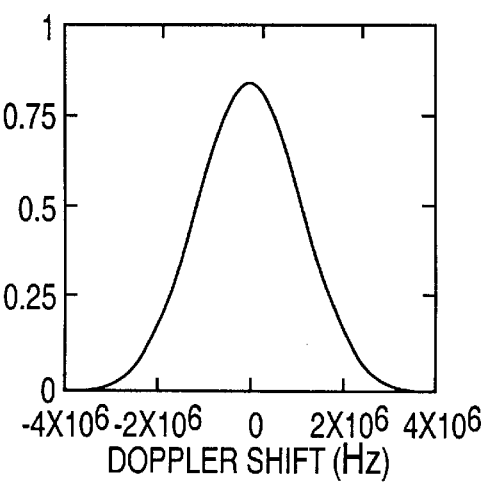

Determining the spectral width of the radiation scattered from the target particle entails assessing the spectral broadening caused by the translational velocity of the target particle and the spectral width of the laser source. As shown in FIG. 1, the drift velocity of a particle is that of its carrier gas in laminar flow in direction 14 and is essentially orthogonal to laser optic axis 68 and to axis 70 of linear array 32 of photodiode detectors 40 and thus contributes no Doppler shift to light scattered from the particle. As a result, to zeroth order there is no Doppler shift associated with the particle drift velocity as configured. To first order, however, the same Maxwell-Boltzmann velocity effects that cause a Doppler-induced frequency spread in the light scattered from the carrier molecules are present in the case of scattering from the target particle. In this case, the frequency spread is dramatically reduced because the much larger mass of the target particles relative to that of a carrier gas molecule. FIG. 3A shows the particle velocity probability density for silicon spheres having a 12.5 nm radius and indicates that the Maxwell-Boltzmann translational velocities associated with the spheres are orders of magnitude smaller than those associated with carrier gas molecules. FIG. 3B shows that the associated Doppler broadening is about three orders of magnitude smaller than that associated with the carrier gas molecules.

The optical system of particle counter 10 of FIG. 1 collects a finite cone of light in the direction along the drift axis, thereby collecting a Doppler-broadened spread in optical frequencies. The amount of this spread may be calculated as follows. For a particle drift velocity, v, and for a half collection angle given by α, the associated Doppler shift is expressed as $$\frac{2v}{\lambda} \times NA, \tag{3}$$

where NA is the effective numerical aperture of the collection optics (NA=sin(α)≈tan(α)≈α in radians for NA<<1) yielding about 0.2 MHz of per meter/second of velocity for NA=0.1. For a drift velocity of one meter/second and an assumed full collection angle below 90 degrees, the associated Doppler shift is less than that of the thermal velocity of the particle and is three orders of magnitude less than the Doppler broadening associated with the background molecular scattering.

The spectral width of laser 12 normally is a limiting factor relating to the quality of a heterodyne or heterodyne laser-based radar system. The Schalow-Townes line width limit is 15 to 16 orders of magnitude smaller than the Doppler broadened Rayleigh molecular scattering described above. The use of miniature-diode-pumped solid-state lasers makes it possible to achieve line widths in the kHz regime. Modern high-Q solid-state lasers should readily achieve line widths of 1 kHz to 1 MHz, which are orders of magnitude smaller than the molecular Doppler broadening associated with background molecular scattering.

The configuration of particle counter 10 shown in FIG. 1 can be made to have nearly identical source-to-detector path lengths for the particle scattered signal and local oscillator. The path difference is preferably designed to be on the order of 10 picoseconds, which is much less than the oscillator round-trip time. The effective line width can, therefore, be nearly zero.

The following is an example of the detection of ultra-small airborne particles. For a wavelength of 0.830 $\mu$m and for an assumed heterodyne efficiency of 0.5, the minimum detectable power for a unity signal-to-noise ratio is $5 \times 10^{-13}$ Watt for an assumed electronic bandwidth of 1 MHz. The 1 MHz bandwidth is comparable to or greater than the laser line width and well beyond the reciprocal of the particle residence time in the laser beam at the velocity specified for Doppler effects induced by the particle drift velocity. Power scattered by polystyrene latex spheres of 0.025 micron diameter is calculated to be $4 \times 10^{-13}$ Watt when the spheres are immersed in an intracavity mode with 100 Watts of recirculating (200 Watts bidirectional) power and the mode diameter is 1.2 mm.

The foregoing presents three significant advantages of the heterodyne detection method over the direct detection method. These advantages include increased particle scattered light signal strength, increased dynamic range, and increased discrimination against background signals. The increased signal strength and dynamic range are independent of carrier gas pressure. The extent of discrimination against background signals depends on the background signal characteristics, which for moderate and high pressure gases is molecular Rayleigh scattering. For low pressure gases (e.g., vacuum gas) molecular scattering is minimal, but discrimination against other background light such as that from process chamber plasma gases or flood lights is realizable.

Figure 5:
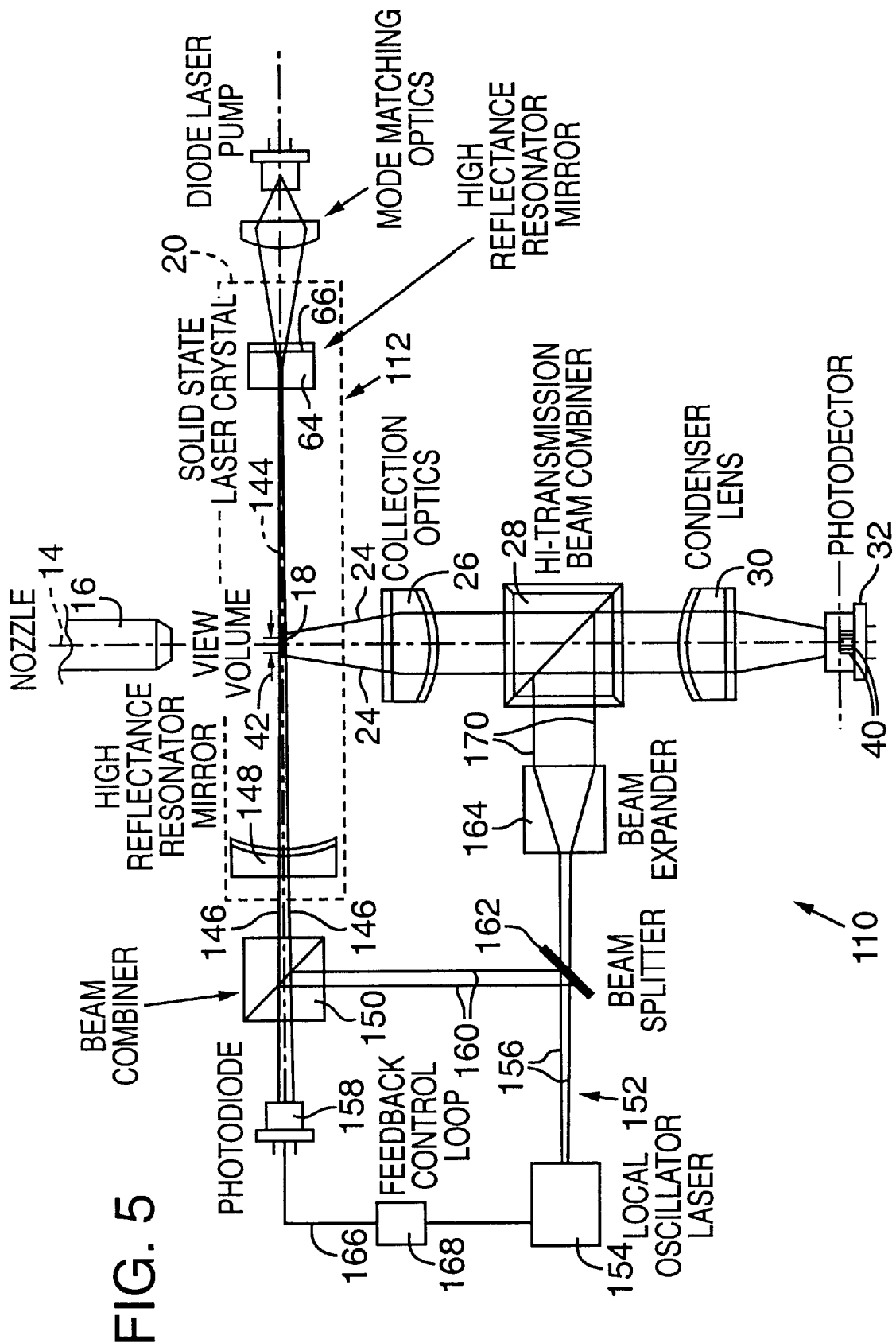
FIG. 5 is a block diagram of an ultra-high sensitivity gas-borne particle counter using multi-channel heterodyne detection and implemented in a dual laser configuration.

FIG. 5 shows a gas-borne particle detector 110 implemented in a dual laser configuration to carry out particle detection using intracavity optical scattering and heterodyne detection techniques. Particle counters 10 and 110 are of similar design; therefore, common optical components are identified by identical reference numerals.

With reference to FIG. 5, particle counter 110 includes a diode laser-pumped, high intracavity power solid-state laser 112, which is robust, efficient, compact, operates in the absence of high voltages, and can be constructed to have the high beam and spectral qualities required for efficient heterodyne detection. The intracavity optical power scatters radiation both from particles injected in a flow direction 14 by a nozzle 16 and from the gases within a view volume 18 in a resonator 20 of laser 112. Scattered light rays 24, including Doppler broadened background Rayleigh light, are collected and collimated by collection optics 26, transmitted through a beam combiner 28, and then imaged by a condenser lens 30, onto a linear array 32 of photodiode detectors 40. Each photodiode detector 40 of array 32 detects the scattered light rays 24 from a small length 42, along an intracavity beam 144 in view volume 18. A small amount of light 146 of very low light power simultaneously leaks out of a very high reflectivity (e.g., 99.999%) left-hand side resonator mirror 148 and strikes a beam combiner 150.

Combiner 150 is an optical component of a feedback control loop 152 that includes a second laser 154, which functions as a local oscillator having a frequency that is different from that of laser 112 by tens of MHz. A single-frequency distributed Bragg reflector diode laser would be a suitable local oscillator laser 154. Control loop 152 maintains a substantially constant frequency difference between lasers 112 and 154 to provide a substantially constant-frequency beat frequency signal that represents the target particle light. Control loop 152 is an automatic feedback system that maintains the substantially constant frequency difference by locking the frequency of local oscillator output beam light rays 156 of laser 154 to a value which is constant relative to the frequency of laser 112. In a configuration in which lasers 112 and 154 are positioned close to each other, control loop 152 accomplishes this result with the use of a photodiode 158 to mix light rays 160, which represent a small fraction of the local oscillator output light rays 156 of laser 154, and the leaked light 146 generated by laser 112. Light rays 160 are directed to photodiode 158 by a beam splitter 162, which reflects light rays 160 toward beam combiner 150 and transmits the remainder of light rays 156 to a beam expander 164. Beam combiner 150 reflects light rays 160 toward photodiode 158.

Photodiode 158 mixes light rays 146 and 160 to produce a beat frequency signal 166 that has a constant amplitude and contains complete information relating to the relative frequency between the outputs of lasers 112 and 154. An automatic controller 168 provides a control voltage signal to control the temperature and/or current of laser 154 to close the control loop and maintain output light rays 156 in frequency lock to light 146 of laser 112.

An expanded beam of light rays 170 propagating through beam expander 164 is directed to beam combiner 28, from which light rays 170 and 24 copropagate to condenser lens 30, where they are focused onto linear array 32 of photodiode detectors 40.

Laser resonator 20 contains a Cr:LiSAF crystal 64 and very high reflectivity (99.999%) curved resonator mirrors 148 and 66 with HR coatings (R~0.999965) to provide high power in a fundamental Gaussian mode. The operational properties of laser resonator 20 are the same as those described for laser 10 of FIG. 1. The heterodyne detection and the counting of small particles are otherwise the same as those described for laser 10 of FIG. 1.

Figure 6:
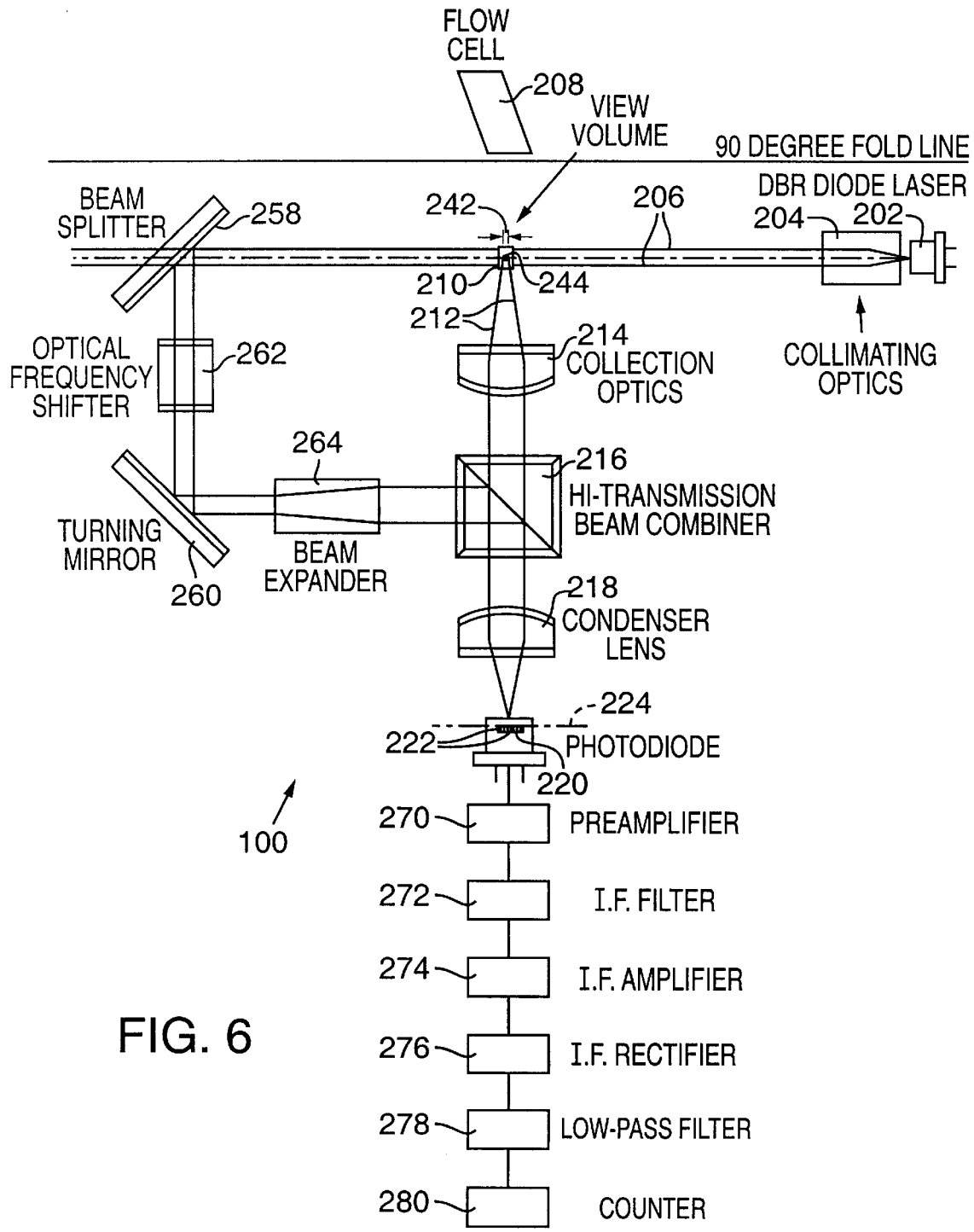
FIG. 6 is a block diagram of an ultra-high sensitivity liquid-borne particle counter using multi-channel heterodyne detection.

Particle detection using external-to-cavity optical scattering and heterodyne detection techniques is described with reference to FIG. 6, which shows a liquid-borne particle counter 200 that performs heterodyne detection of small particles. Particle counter 200 includes a distributed Bragg reflector diode laser 202 operating in single transverse mode and single longitudinal mode at preferably 852 nm wavelength and 150 mW power. The light output of laser 202 propagates through collimating optics 204 to form a 0.2 mm diameter collimated beam of light rays 206 that pass through a water (or other liquid) flow cell 208 oriented at the Brewster angle relative to the beam of light rays 206. (The 90 Degree Fold Line identified in FIG. 6 indicates that liquid flows through flow cell 208 in a direction outwardly of the plane of FIG. 6.) Because the internal and external Brewster angles are unequal for certain flow cell models, the Brewster angle selected represents a compromise that minimizes feedback to diode laser 202, maximizes transmission through flow cell 208, and minimizes the amount of reflected light scattered within the flow cell channel. The optical power scatters radiation from particles carried by the liquid flowing through flow cell 208 within a view volume 210. Scattered light rays 212, including Brillouin broadened background light are collected and collimated by collection optics 214, transmitted through a beam combiner 216, and then imaged by a condenser lens 218 onto a linear array 220 of photodiode detectors 222 positioned on an axis 224. Each photodiode detector 222 of array 220 detects the scattered light rays 212 from a small length 242 along an external cavity beam 244 in view volume 210.

A portion of light rays 206 propagates through flow cell 208 unscattered and is redirected by a beam splitter 258 and a turning mirror 260. Beam splitter 258 reduces the intensity of the portion of light rays 206 striking turning mirror 260 to prevent saturation of photodiode detectors 222, to which the portion of light rays 206 is directed as described below. An optical frequency shifter 262 positioned between beam splitter 258 and turning mirror 260 frequency shifts the unscattered portion of light rays 206 by about 21.4 MHz to form a local oscillator light signal, which is collimated and expanded by a beam expander 264. The local oscillator light signal propagates from beam expander 264 to beam combiner 216, from which local oscillator light signal and scattered light rays 212 collinearly copropagate to condenser lens 218 where they are focused onto linear array 220 of photodiode detectors 222.

Thus, in accordance with the technique described above for gas-borne particle counter 10 implementing a self-heterodyne or "homodyne" method, light rays 212 scattered by particles in flow cell 208 are collected and combined with the local oscillator light signal. The combined light beam is focused on a square-law photodiode detector 222, where optical mixing takes place. Optical electrical current produced by photodiode detector 222 is converted into a voltage amplified by a preamplifier 270. An IF filter 272, with a 4.2 MHz bandwidth centered at 21.4 MHz, filters most of the liquid-caused Brillouin scattering background, 1/f noise, and part of the shot noise. An amplifier 274 amplifies the output signal from IF filter 272 before the output signal is rectified at a rectifier 276 and processed to recover the particle-scattered signal envelope in low pass filter 278, which in combination reduces the shot noise by a factor of 4.2 MHz/20 kHz=210. The recovered signal is counted by a counting device 280, which includes an analog-to-digital converter.

Although the local oscillator shot noise is the dominant component among various types of noises by the nature of the homodyne detection technique, three types of background scattered light in liquid sensor 208 are considered to make appropriate assessment of the optical signals and to determine the required level of the local oscillator power. Significant background noise may stem from the walls and windows of liquid flow cell 208, which scatters a certain amount of light because of imperfect surfaces. Flow cell 208 is designed such that the light scattered from the walls is minimum while the light scattered from the windows can be blocked by spatial filters. The other two types of background light are Rayleigh and Brillouin scattering of the water. The Rayleigh band represents the scattering of light by the water entropy or heat fluctuations. The Brillouin doublets are caused by inelastic interactions between laser photons and hydrodynamic modes of the water, in which the photons gain or lose energy to the photons and thereby undergo frequency shifts. The intensity ratio between the Rayleigh and Brillouin bands is given by $$\frac{I_R}{2I_B} = \frac{c_p}{c_v} - 1, \quad (4)$$

where $c_p$ and $c_v$ are the specific heat at constant p (pressure) and constant v (volume), respectively. For water, $c_p$=$c_v$; thus the Rayleigh scattering is quite weak and its bandwidth is 32.8 MHz, which is eight times larger than the particle-scattered signal bandwidth. As a result, the background arising from Rayleigh scattering is minimal. The intensity of the water Brillouin scattering is strong; therefore, a relatively high intensity local oscillator is needed to overcome the shot noise caused by Brillouin scattering. This condition can be readily achieved by the preferred external cavity configuration of FIG. 6. According to literature, the minimum frequency shift of water Brillouin scattering is 6.28 GHz. The high background arising from the Brillouin scattering in the output of photodiode detector 222 can be completely rejected by IF filter 272, the bandwidth of which is 4.2 MHz.

The following is an example of the detection of ultra-small liquid-borne particles. For a liquid flow speed of 2.6 meters per second through a Model 47F-Q-10 flow cell manufactured by Stama Cells, Inc. and a collection angle of 45 degrees, the Doppler broadened line width of the particle-scattered light is 1.2 MHz, which is smaller than the 3 MHz laser instantaneous line width specified for a Model 5712-H1 laser diode, manufactured by SDL, Inc. A homodyne efficiency of 0.5 gives a $5 \times 10^{-19}$ Watt/Hz minimum detectable signal power for a signal-to-noise ratio of 1.0, computed in accordance with Equation (2). For a 4.2 MHz bandwidth of IF filter 272, the minimum detectable power is $2 \times 10^{-12}$ Watt. Low pass filter 278 following rectifier 276 further reduces the shot noise and thereby reduces minimum detectable signal to $9 \times 10^{-15}$ Watt. The light scattered from a 0.04 $\mu$m diameter particle has an expected intensity of $3 \times 10^{-14}$ Watt, which is higher than the minimum detectable power by a power of three. A size sensitivity of 0.04 $\mu$m is therefore achievable.

It will be obvious to those having skill in the art that many changes may be made to the details of the above-described embodiments of this invention without departing from the underlying principles thereof. For example, a dual laser configuration could also be implemented in liquid-borne particle detection. The scope of the present invention should, therefore, be determined only by the following claims.

We claim:

1. A dual coherent radiation source-based optical scattering method of achieving high sensitivity fluid-particle detection in the presence of a background radiation signal level, comprising:

introducing into a view volume target particles immersed in a fluid carrier, the fluid carrier having molecules with a spectral scattering characteristic;

causing coherent radiation having a first predetermined frequency emitted by a first source to propagate through the view volume, at least a portion of the coherent radiation propagating through the view volume striking the target particles and thereby forming a scattered portion of the radiation, the scattered portion of the radiation exiting the view volume;

causing coherent radiation having a second predetermined frequency to propagate from a second source, the second predetermined frequency being different by a substantially constant amount from the first predetermined frequency;

collecting the scattered portion of the radiation; and directing the coherent radiation having a second predetermined frequency and the collected scattered portion of the radiation to strike a radiation-sensitive detector to create a substantially constant-frequency beat frequency signal that represents a property of the target particles by diminishing the spectral scattering characteristic of the fluid carrier and thereby reducing the background radiation signal level.

2. The method of claim 1 in which the introducing of target particles includes directing a flow stream of the target particles immersed in a fluid carrier in a direction transverse to the coherent radiation propagating through the view volume.

3. The method of claim 1 in which the view volume is included within a laser cavity and the fluid carrier includes a gas.

4. The method of claim 1 in which the coherent radiation of a first predetermined frequency is produced by a first laser, the view volume is positioned external to the first laser and is included within a liquid flow cell, and the fluid carrier includes a liquid.

5. The method of claim 4 in which the first laser comprises a diode laser.

6. The method of claim 1 in which a radiation beam combiner superimposes the collected scattered portion and the coherent radiation having a second predetermined frequency before they strike the radiation detector.

7. The method of claim 6 in which the radiation-sensitive detector comprises a photodiode.

8. The method of claim 1 in which the radiation-sensitive detector comprises a linear array of radiation-sensitive elements that form multiple parallel detection channels.

9. The method of claim 1 in which the property of the target particles is their sizes.

10. The method of claim 1 in which the property of the target particles is the number of the target particles as represented by occurrences of the beat frequency signal.

11. The method of claim 1 in which the substantially constant amount is effected by achieving a frequency lock of the second source to a value that is substantially constant relative to the first predetermined frequency of the first source.

12. A heterodyne optical fluid-particle detection system implemented with separate coherent radiation sources, comprising:

a flow region through which a stream of target particles immersed in a carrier fluid passes, the flow region having a view volume through which the carrier fluid flows in a flow direction;

a first source of coherent radiation having a first predetermined frequency and directed to propagate through the view volume in transverse direction to the flow direction of the carrier fluid, the target particles scattering a quantity of the coherent radiation propagating through the view volume so that target particle-scattered radiation exits the view volume, the target particle-scattered radiation having a signal strength;

a second source of coherent radiation having a second predetermined frequency that is different by a substantially constant amount from the first predetermined frequency;

an optical beam combiner receiving and combining the target particle-scattered radiation and the coherent radiation propagating from the second source and not scattered by the target particles to form a combined beam; and a radiation-sensitive detector receiving the combined beam, the radiation-sensitive detector creating a substantially constant-frequency beat frequency signal that represents a property of the target particles, the beat frequency signal having increased signal strength relative to the target particle-scattered radiation signal strength and thereby increasing the signal-to-noise ratio of the particle detection system.

13. The system of claim 12 in which the first source of coherent radiation comprises a laser that includes a laser cavity, the flow region is included within the laser cavity, and the fluid carrier includes a gas.

14. The system of claim 12 in which the flow region is positioned external to the first source of coherent radiation and is included within a liquid flow cell.

15. The system of claim 14 in which the first source of coherent radiation includes a diode laser.

16. The system of claim 12 in which the radiation-sensitive detector comprises a photodiode.

17. The system of claim 12 in which the radiation-sensitive detector comprises a linear array of radiation-sensitive elements that form multiple parallel detection channels.

18. The system of claim 12 in which the property of the target particles is their sizes.

19. The system of claim 12 in which the property of the target particles is the number of the target particles as represented by occurrences of the beat frequency signal.

20. The system of claim 12, further comprising a feedback control loop in which the second source of coherent radiation functions as a local oscillator and responds to the coherent radiation propagating from the first source to achieve frequency lock to a value that is substantially constant relative to the first determined frequency of the first source and thereby establish the substantially constant amount of difference between the first and second predetermined frequencies.

* * * * *